(12) United States Patent
Cutler

(10) Patent No.: US 6,187,790 B1
(45) Date of Patent: Feb. 13, 2001

(54) USE OF CILOSTAZOL FOR TREATMENT OF SEXUAL DYSFUNCTION

(75) Inventor: Neal R. Cutler, 10464 Sunset Blvd., Los Angeles, CA (US) 90077

(73) Assignee: Neal R. Cutler, Los Angeles, CA (US)

( * ) Notice: Under 35 U.S.C. 154(b), the term of this patent shall be extended for 0 days.

(21) Appl. No.: 09/262,715

(22) Filed: Mar. 4, 1999

(51) Int. Cl.[7] ................................................ A61K 31/47

(52) U.S. Cl. .......................................................... 514/312
(58) Field of Search ............................................. 514/312

(56) References Cited

U.S. PATENT DOCUMENTS

| | | |
|---|---|---|
| 1,897,423 | 2/1933 | Ferri . |
| 2,584,166 | 2/1952 | Stevenson et al. ............ 167/64 |
| 2,696,209 | 12/1954 | Varaney ......................... 128/132 |
| 3,373,746 | 3/1968 | White et al. .................... 128/294 |
| 4,277,479 | 7/1981 | Nishi et al. ..................... 424/258 |
| 4,311,707 | 1/1982 | Birnbaum et al. ............. 424/305 |
| 4,478,822 | 10/1984 | Haslam et al. .................. 424/78 |
| 4,552,891 | 11/1985 | Ho et al. ......................... 514/443 |
| 4,610,868 | 9/1986 | Fountain et al. ............... 424/1.1 |
| 4,640,912 | 2/1987 | Hausman ........................ 514/54 |
| 4,746,508 | 5/1988 | Carsey et al. ................... 424/88 |
| 4,801,587 | 1/1989 | Voss et al. ...................... 514/248 |
| 4,829,991 | 5/1989 | Boeck ............................. 128/79 |
| 5,270,323 | 12/1993 | Milne, Jr. et al. ............. 514/309 |
| 5,393,773 | 2/1995 | Craig et al. ..................... 514/415 |
| 5,447,912 | 9/1995 | Gerstenberg et al. .......... 514/12 |
| 5,474,535 | * 12/1995 | Place et al. ..................... 604/60 |
| 5,492,911 | 2/1996 | Stief ................................ 514/252 |
| 5,554,639 | 9/1996 | Craig et al. ..................... 514/415 |
| 5,603,943 | 2/1997 | Yanagwa ......................... 424/434 |
| 5,627,191 | 5/1997 | Birch et al. ..................... 514/303 |
| 5,719,197 | 2/1998 | Kanios et al. ................... 514/772.6 |
| 5,721,238 | 2/1998 | Heiker ............................. 514/259 |
| 5,773,457 | 6/1998 | Nahoum ......................... 514/397 |
| 5,801,161 | 10/1998 | Merkus .......................... 514/52 |
| 5,864,037 | 1/1999 | Chasin et al. .................. 544/118 |
| 5,869,479 | 2/1999 | Kreutner et al. ............... 514/212 |

FOREIGN PATENT DOCUMENTS

| | | |
|---|---|---|
| 0 357 581 B2 | 7/1990 | (EP) ............................. A61K/47/00 |
| 94/28902 | 12/1994 | (WO) . |

OTHER PUBLICATIONS

MEDLINE abstract, AN: 86077114, Akiyama et al., Arzneimittel–Forschung (1985), 35, 7A, pp. 1124–1132.*

Dawson et al., "Cilostazol has Beneficial Effects in Treatment of Intermittent Claudication," *Circulation* 98: 678–686 [1998].

Delcour et al., "Impotence: Evaluation with Cavernosography," *Radiology* 161:803–806(1986).

Micromedex Inc., Drug Evaluation Monographs, vol. 99, Feb. 28, 1999.

Shimizu et al., "Physico–chemical Properties and Stability of Cilostazol," *Arzneim.–Forsch*.35: 1117–1123 (1985).

Akiyama et al., "The Absorption, Distribution and Excretion of a New Antithrombotic and Vasodilating Agent, Cilostazol, in Rat, Rabbit, Dog and Man," *Arzneim.–Forsch*.35: 1124–1132 (1985).

Akiyama et al., "The Metabolism of a New Antithrombotic and Vasodilating Agent, Cilostazol, in Rat, Dog and Man," *Arzneim.–Forsch*.35: 1133–1140 (1985).

Usuda et al., "The Localization of a New Antithrombotic Agent, Cilostazol, in CHO–K1 Cells as Demonstrated by Autoradiography," *Arzneim.–Forsch*.35: 1141–1143 (1985).

Kimura et al., "Effect of Cilostazol on Platelet Aggregation and Experimental Thrombosis," *Arzneim.–Forsch*.35: 1144–1149 (1985).

Kawamura et al., "Effect of Cilostazol, a New Antithrombotic Drug, on Cerebral Circulation," *Arzneim.–Forsch*.35: 1149–1153 (1985).

Kawamura et al., "Effect of Cilostazol, a New Antithrombotic Drug, on an Experimental Model of Peripheral Circulation Insufficiency," *Arzneim.–Forsch*.35: 1154–1156 (1985).

Shintani et al., "General Pharmacological Properties of Cilostazol, a New Antithrombotic Drug," *Arzneim.–Forsch*.35: 1157–1162 (1985).

Shintani et al., "General Pharmacological Properties of Cilostazol, a New Antithrombotic Drug," *Arzneim.–Forsch*.35: 1163–1172 (1985).

Niki and Mori, "Phase I Study of Cilostazol. Safety evaluation at increasing single doses in healthy volunteers," *Arzneim.–Forsch*. 35: 1173–1185 (1985).

Yasunaga et al., "Clinical Effects of Oral Cilostazol on Suppression of Platelet Function in Patients with Cerebrovascular Disease," *Arzneim.–Forsch*.35: 1186–1188 (1985).

Yasunaga et al., "Antiaggregatory Effects of Oral Cilostazol and Recovery of Platelet Aggregability in Patients with Cerebrovascular Disease," *Arzneim.–Forsch*.35: 1189–1192 (1985).

Kobayashi et al., "Long–term Effects of Cilostazol on Cerebral Blood Flow in Chronic Cerebral Infarction," *Arzneim.–Forsch*.35: 1193–1197 (1985).

Yasuda et al., "Hemodynamic Effects of Cilostazol on Increasing Peripheral Blood Flow in Arteriosclerosis obliterans," *Arzneim.–Forsch*.35: 1198–1200 (1985).

(List continued on next page.)

*Primary Examiner*—Theodore J. Criares
*Assistant Examiner*—Jennifer Kim
(74) *Attorney, Agent, or Firm*—Medlen & Carroll, LLP

(57) ABSTRACT

Methods for treating specific patient groups for sexual dysfunction are provided. The methods of the present invention comprise the utilization of cilostazol and pharmaceutical compositions comprising cilostazol in patients. In one embodiment, patients are free of cardiac disease. In other embodiments, patients have not been treated with a drug that causes hypotensive effects, and/or who have not been given organic nitrites or nitrates. Cilostazol and pharmaceutical compositions of cilostazol are administered to patients orally, cutaneously, transurethrally, intracavemosally, by injection, intranasally, or through respiratory inhalation.

17 Claims, No Drawings

OTHER PUBLICATIONS

Kamiya et al., "Hemodynamic Effects of the Antithrombotic Drug Cilostazol in Chronic Arterial Occlusion in the Extremities," *Arzneim.–Forsch.*35: 1201–1203 (1985).

Ohashi et al., "Thermographic Evaluation of the Hemodynamic Effects of the Antithrombotic Drug Cilostazol in Peripheral Arterial Occlusion," *Arzneim.–Forsch.*35: 1203–1208 (1985).

Lue et al., "Physiology of Erection and Pharmacological Management of Impotence," *J. Urol.* 37:829–836 (1987).

Nishi et al., "Studies on 2–Oxoquinoline Derivatives as Blood Platelet Aggregation Inhibitors. II. 6–[3–(1–Cyclohexyl–5–tetrazoly)propoxy]–1, 2–dihyrdo–2–oxoquinoline and Related Compounds," *Chem. Pharm. Bull.* 31: 1151–1157 [1983].

Porst et al., "Relevance of Dynamic Cavernosography to the Diagnosis of Venous Incompetence in Erectile Dysfunction," *J. Urol.* 137:1163–1167 (1987).

Suri et al., "Pharmacokinetics of Multiple–Dose Oral Cilostazol in Middle–Age and Elderly Men and Women," *J. Clin. Pharmacol.* 38: 144–150 [1998].

Garban et al., "Effect of aging on nitric oxide–mediated penile erection in rats," *Am. J. Phys.* 46:H467–H475 (1995).

Rajfer et al., "Nitric Oxide as a Mediator of Relaxation of the Corpus Cavernosum in Response to Nonadrenergic, Noncholinergic Neurotransmission," *New Engl. J. Med.* 326:90–94 (1992).

Boolel et al., "Sildenafil, a novel effective oral therapy for male erectile dysfunction," *Br. J. Ur.* 78:257–261 (1996).

Silver et al., "Differential pharmacologic sensitivity of cyclic nucleotide phosphodiesterase isozymes isolated from cardiac muscle, arterial and airway smooth muscle," *European J. Pharmacology,* 150:85–94 (1988).

Kauffman et al., "Characterization and Pharmacological Relevance of High Affinity Binding Sites for [$^3$H] LY186126, a Cardiotonic Phosphodiesterase Inhibitor, in Canine Cardiac Membranes," *Circulation Research,* 65(1):154–163 (1989).

Malhotra et al., "Cavernosography in conjuction with artificial erection for evaluation of venous leakage in impotent men," *Radiology,* 161(3):799–802 (1986).

Minami et al., "Inhibition of shear–induced platelet aggregation by cilostazol, a specific inhibitor of cGMP–inhibited phosphodiesterase, in vitro and ex vivo" *Life Sciences,* 61(25):383–389 (1997).

Shiraishi et al., "Effect of cilostazol, a phosphodiesterase type III inhibitor, on histamine–induced increase in [$Ca^{2+}$]$_i$ and force in middle cerebral artery of the rabbit" *British Journal of Pharmacology,* 123:869–878 (1998).

* cited by examiner

USE OF CILOSTAZOL FOR TREATMENT OF SEXUAL DYSFUNCTION

FIELD OF THE INVENTION

The present invention relates to methods for the treatment of sexual dysfunction in males and females (including but not limited to erectile dysfunction in males).

BACKGROUND

Impotence or erectile insufficiency is a widespread disorder that is thought to affect about twelve percent of adult men under age forty-five, about twenty percent of men at age sixty, and about fifty-five percent of men at age seventy-five. Similar to male sexual dysfunction, the prevalence of female sexual dysfunction has been shown to increase with age and be associated with the presence of vascular risk factors and the development of menopause.

There is more than one cause of erectile dysfunction. For example, erectile dysfunction can be psychological, resulting from anxiety or depression, with no apparent somatic or organic impairment. Such erectile dysfunction, which is referred to as "psychogenic", is responsible for about fifteen to twenty percent of cases of impotence. In other cases, the erectile dysfunction is associated with atherosclerosis of the arteries supplying blood to the penis; such dysfunction is referred to as "arteriogenic" or "atherosclerotic." About forty to sixty percent of cases of impotence are arteriogenic in origin.

In still other cases, there is leakage from veins in the penis such that sufficient pressure for an erection can be neither obtained nor maintained. This dysfunction is referred to as "venous leakage," or "abnormal drainage". This condition is often exacerbated by the presence of some arteriogenic dysfunction whereby the supply of blood to the penis is impaired. In still other cases, the dysfunction is associated with a neuropathy, such as nerve damage arising from, for example, surgery or a pelvic injury, in the nervous system affecting the penis. Such a dysfunction is referred to as "neurogenic" and this accounts for about ten to fifteen percent of cases of impotence.

There is also a high incidence of erectile insufficiency among diabetics, particularly those with insulin-dependent diabetes mellitus. Erectile dysfunction in diabetics is often classified as "diabetogenic," although the underlying dysfunction is usually neurogenic associated with neuropathy, but may be arteriogenic or neurogenic and arteriogenie. About half of diabetic males suffer from erectile insufficiency, and about half of the cases of neurogenic impotence are in diabetics.

Additionally, erectile insufficiency is sometimes a side effect of certain drugs, such as beta-blockers that are administered to reduce blood pressure in persons suffering from hypertension, or drugs administered to treat depression or anxiety. Excessive alcohol consumption has also been linked to erectile insufficiency. These forms of erectile insufficiency may be regarded as a subset of neurogenic or psychogenic insufficiency.

A number of methods to treat impotence are available. These treatments include pharmacological treatments, surgery and, in cases of psychogenic dysfunction, psychological counseling is sometimes effective. Psychogenic impotence often can be cured by counseling coupled with a demonstration to the patient that he is capable of having a full erection by inducing such an erection once or a few times in the patients. Insufficiency due to excessive alcohol consumption is sometimes cured by reducing or elimination such consumption.

In rare cases, where the insufficiency is physical because of venous leakage, surgery can usually be employed to repair the venous lesion and thereby either cure the insufficiency or, if there remains an erectile insufficiency after repair of the venous lesion, render the insufficiency amenable to treatment by pharmacological methods. Also, penile implants, which provide a mechanical means to produce an erection sufficient for vaginal penetration, are widely used to treat impotence. In recent years, implants have been employed, especially in cases where pharmacological intervention is ineffective, which are usually cases of severe atherogenic impotence. Treatment of impotence with penile implants, however, entails serious disadvantages. Such treatment requires surgery and necessitates total destruction of the erectile tissues of the penis, forever precluding normal erection.

Pharmacological methods of treatment are also available. Such methods, however, have not proven to be highly satisfactory and can be accompanied by severe side-effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a smooth muscle relaxant, or phenoxybenzamine, a non-specific blocker and hypotensive, into a corpus cavernosum has been found to cause an erection sufficient for vaginal penetration. Also, in cases where severe atherosclerosis is not a cause of the dysfunction, intracavernosal injection of phentolamine, an α-adrenergic blocker, causes an erection sufficient for vaginal penetration. The resulting erection is one of significantly shorter duration than that induced by intracavernosal injection of papaverine or phenoxybenzamine and is of such short duration that satisfactory sexual relations are difficult or impossible.

Treatment of impotence with papaverine or phenoxybenzamine often results in priapism, a locking-up of an erection for a long period of time, typically a few hours and sometimes longer than twenty-four hours. Priapism is a serious, deleterious side effect of treatment of erectile insufficiency with these drugs. Beyond the embarrassment that may be caused for some men, priapism is usually painful, irreversibly damages erectile tissue, and, to be relieved, requires bleeding or pharmacological intervention, such as injection of a sympathomimetic drug, such as adrenaline.

Even if priapism does not occur with use of papaverine, such use is associated with a painful, burning sensation in the first two or so minutes after the injection and there are indications that repeated use of papaverine causes undesirable, extensive intracavernous fibrosis. Further, as indicated above, impotence arising from severe atherosclerosis is not susceptible to treatment with papaverine, phenoxybenzamine, phentolamine or papaverine together with phentolamine. In any case, phenoxybenzamine is not suitable for use in treating impotence because it is a carcinogen.

Thus, although impotence is a ubiquitous problem, there are few satisfactory methods available for treating this disorder. Because of the relatively invasive intervention involved and the high failure rate of penile prostheses, surgical approaches provide unattractive alternatives. A safe pharmacological approach to the treatment of impotence is still to be achieved.

What is needed is a pharmaceutical that is effective but lacking in significant side effects.

SUMMARY OF THE INVENTION

The present invention relates to methods for the treatment of sexual dysfunction in males and females (including but not limited to erectile dysfunction in males). While the present invention is not limited to treatment of a particular patient group, it is contemplated that the methods of the present invention comprise the utilization of pharmaceutical compounds and compositions to patients who are free of symptoms of cardiac disease and who have not been treated with drugs which cause hypotensive effects, such as nitrites and nitrates. The compositions comprise quinolines, including derivatives and metabolites thereof.

It is not intended that the present invention be limited by the nature of the derivative. In a preferred embodiment, the quinoline is an oxoquinoline. In yet another preferred embodiment, the oxoquinoline is cilostazol (6-[4-(1-cyclohexyl-1-H-tetrazol-5-yl)butoxyl]-3,4-dihydro-2(1H)-quinolinone; 6-[4-(1-cyclohexyl-1-H-tetrazol-5-yl)butoxy]-3,4-dihydrocarbostyril; 6-[4-(1-cyclohexyl-5-tetrazoyl) butoxy]-1,2,3,4-tetrahydro-2-oxoquinoline).

In yet other preferred embodiments, metabolites of cilostazol are contemplated for use in the methods of the presently claimed invention. Metabolites of cilostazol include, but are not limited to monohydroxycilostazol, monohydroxydehydrocilostazol, 3,4-dihydro-6-hydroxy-2 (1H)-quinolinone, their conjugates and dehydrocilostazol.

In one embodiment, the method comprises a) providing: i) a patient (whether male or female) suffering from symptoms of sexual dysfunction; and ii) cilostazol; and b) administering cilostazol to the patient such that such symptoms are reduced. It is not intended that the present invention be limited to the mode of administration. In one embodiment, cilostazol is administered orally. In another embodiment, cilostazol is administered cutaneously. In yet another embodiment, cilostazol is administered intranasally. In an alternative embodiment, cilostazol is administered through respiratory inhalation. In yet another alternative embodiment, cilostazol is administered by standard injection.

In one embodiment, cilostazol is administered as a tablet. In another embodiment, cilostazol is administered as a pharmaceutical composition. In yet another embodiment, cilostazol is administered as a single dosage of 100 milligrams per day.

It is not intended that the present invention be limited to the treatment of certain patient groups. In one embodiment, the patient is male. In another embodiment, the patient is female. In one embodiment, the patient is free from cardiac disease. In another embodiment, the patient has not been treated with a drug that causes hypotensive effects. In yet another embodiment, the patient has not been treated with nitrates or nitrites.

In another embodiment, the method comprises providing: i) a male with erectile dysfunction, and ii) a pharmaceutical composition comprising cilostazol; and introducing the pharmaceutical composition to the male such that an erection is produced.

It is not intended that the present invention be limited by the method of introduction of cilostazol. In one embodiment, the cilostazol is introduced into the male orally. In a preferred embodiment, the male is an adult human and the oral dosage is in a single dose per day of 100 milligrams.

The present invention is not limited by the degree of response by the male subject. In one embodiment, the erection induced is sufficient for vaginal penetration.

Likewise, the present invention also contemplates the use of sexual stimulation in addition to the application of a pharmaceutical composition. For example, one embodiment comprises a) providing: i) a male, having a penis, with erectile dysfunction, ii) cilostazol, and iii) sexual stimulation; and b) introducing said cilostazol and sexual stimulation to the male such that an erection is produced. In another embodiment, the method comprises a) providing: i) a male, having a penis, with erectile dysfunction, ii) a pharmaceutical composition comprising cilostazol, and iii) sexual stimulation; and b) introducing said cilostazol and sexual stimulation to the male such that an erection is produced.

Likewise, the present invention is not limited by the nature of the sexual stimulation. In one embodiment, the sexual stimulation is sexually explicit media. In another embodiment, the sexual stimulation involves manipulation of the penis, such as with vibration.

It is not intended that the present invention be limited by the nature of the formulation. In one embodiment, the present invention contemplates a formulation comprising a quinoline or derivative thereof in a mixture comprising lactose.

DEFINITIONS

As used herein, the term "quinoline" refers to chemical compositions comprising quinoline as set forth in the following structure:

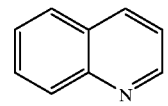

as well as other forms of quinoline (e.g., 2-oxoquinoline):

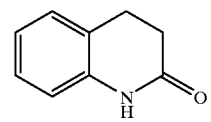

As used herein, "cilostazol" refers to a chemical compound as set forth in the following structure:

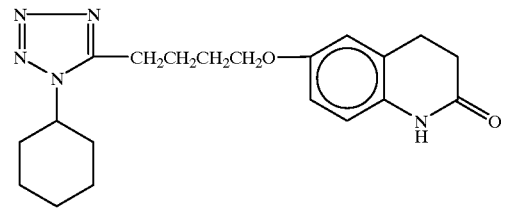

As used herein, a patient who is "free from cardiac disease" and a patient who is "free from symptoms of cardiac disease" indicate that the patient has not been diagnosed with angina, myocardial infarction, congestive heart failure and that symptoms of angina, ischemia, myocardial infarction, congestive heart failure have not been detected, respectively.

As used herein, "drugs that have hypotensive effects" are those drugs which, when administered, cause the patient's end-diastolic blood pressure to be reduced. Nitrates are commonly used drugs which have hypotensive effects.

As used herein, "nitrates" are compounds that contain the —$NO_3$—moiety. Nitrates typically used in the clinic are shown in Table 1.

As used herein, "nitrites" are compounds that contain the —NO₂—moiety. Nitrites typically used in the clinic are shown in Table 1.

As used herein, the term "erectile dysfunction" refers to certain disorders of the cavernous tissue of the penis and the associated facia which produce impotence, the inability to attain a sexually functional erection.

As used herein "standard injection" refers to the placement of a pharmaceutical composition into a subject (e.g., with a hypodermic needle). For example, such injection can be made subcutaneously, intravenously, intramuscularly, intracavernosally, etc.

As used herein, "by oral administration" refers to the introduction of a pharmaceutical composition into a subject by way of the oral cavity (e.g., in aqueous liquid or solid form).

As used herein, "cutaneously" refers to the introduction of a pharmaceutical composition into a subject by application to the surface of the skin such that the composition is absorbed into the subject.

As used herein, "transurethrally" refers to the introduction of a pharmaceutical composition to the urethra of a subject such that the composition is absorbed into the subject.

As used herein, "intranasally" refers to the introduction of a pharmaceutical composition within the nasal cavity.

TABLE 1

Organic Nitrates Available for Clinical Use

| NONPROPRIETARY NAMES AND TRADE NAMES | CHEMICAL STRUCTURE | PREPARATIONS, USUAL DOSES, AND ROUTES OF ADMINISTRATION* |
|---|---|---|
| Amyl nitrite (isoamyl nitrite) | 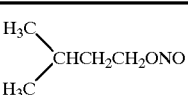 | Inh: 0.18 or 0.3 ml, inhalation |
| Nitroglycerin (glycerol trinitrate; NITRO-BID, NITROSTAT, NITROL, NITRO-DUR, others) | 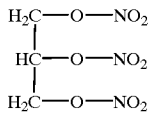 | T: 0.15 to 0.6 mg as needed<br>S: 0.4 mg per spray as needed<br>C: 2.5 to 9 mg two to four times daily<br>B: 1 mg every 3 to 5 h<br>O: 1.25 to 5 cm (½ to 2 in.), topically to skin every 4 to 8 h<br>D: 1 disc (2.5 to 15 mg) every 24 h<br>IV: 5 µg/min; increments of 5 µg/min |
| Isosorbide dinitrate (ISORDIL, SORBITRATE, DILATRATE, others) | 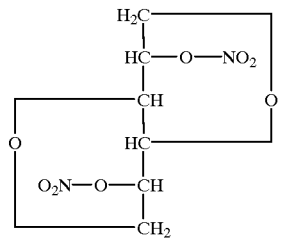 | T: 2.5 to 10 mg every 2 to 3 h<br>T(C): 5 to 10 mg every 2 to 3 h<br>T(O): 10 to 40 mg every 6 h<br>C: 40 to 80 mg every 8 to 12 h |
| Isosorbide-5-mononitrate (IMDUR, ISMO, others) | 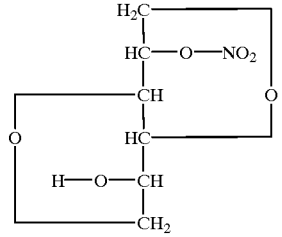 | T: 10 to 40 mg twice daily<br>C: 60 mg daily |
| Erythrityl tetranitrate (CARDILATE) | 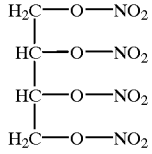 | T: 5 to 10 mg as needed<br>T(O): 10 mg three times daily |

*B, buccal (transmucosal) tablet; C, sustained-release capsule or tablet; D, transdermal disc; Inh, inhalant; IV, intravenous injection; O, ointment; S, lingual spray; T, tablet for sublingual use; T(C), chewable tablet; T(O), oral tablet or capsule.

As used herein, "intracavernosal" injection is injection into the corpus cavernosum of the penis.

As used herein, an "erection" refers to the condition of a penis whereby it is at least semi-rigid as opposed to being in a flaccid state.

As used herein, "respiratory inhalation" refers to the introduction of a pharmaceutical composition within the respiratory tract.

As used herein, "sufficient for vaginal penetration" refers to the state of an erection such that the penis is capable of entering a vagina without manual manipulation.

As used herein, "sexual stimulation" refers to activity that would induce an erection in a male without erectile dysfunction (e.g., sexually explicit media, manual manipulation, vibration, live erotic entertainment, etc.)

As used herein, "sexually explicit media" refers to films, videos, books, magazines, etc. that depict sexual activity.

As used herein "single dosage" refers to a pharmaceutical composition of a formulation that is capable of achieving its intended effect in a single application.

DETAILED DESCRIPTION OF THE INVENTION

The present invention relates to methods for the treatment of sexual dysfunction in males and females (including but not limited to erectile dysfunction in males). The compositions comprise quinolines, including derivatives thereof.

In one embodiment, the present invention contemplates the use of compositions that are effective to induce an erection in a human male suffering from impotence of any origin, other than anatomical deficiencies (i.e., lacking a penis or a significant portion thereof) that preclude an erection sufficient for vaginal penetration. In particular, these compositions may be used to induce an erection in a male suffering from impotence caused by severe atherosclerosis, and also impotence that is neurogenic or psychogenic in origin. The compositions utilized in the methods of the present invention comprise cilostazol, including derivatives thereof.

Cilostazol is a phosphodiesterase inhibitor (type III) that suppresses platelet aggregation and also acts as a direct arterial vasodilator. In addition to its reported vasodilator and antiplatelet effects, cilostazol has been proposed to have beneficial effects on plasma lipoproteins, increasing plasma high density lipoprotein cholesterol and apoliproprotein (See e.g., Dawson et al., Circulation 98: 678–686 [1998]; Elam et al., Arterioscler Thromb. Vasc. Biol. 18: 1942–1947 [1998]; Drug Evaluation Monographs, vol. 99, Micromedex Inc.).

Method of preparation of cilostazol are set forth by Nishi et al. (Chem. Pharm. Bull. 31: 1151[1983], and U.S. Pat. No. 4,277,479, hereby incorporated by reference), and its pharmacology, metabolism, mechanism of action and clinical evaluations are described in Arzneimittel-Forsch. 35: 1117–1208 (1985), hereby incorporated by reference. While it is not necessary to understand any particular mechanism to carry out the present invention, it is believed that in some circumstances cilostazol can act as a direct-acting vasodilator to relax the corpus cavernosum smooth muscle cells, which in turn increases blood flow into the cavernosa space. This then leads to increased cavernosa pressure to produce an erect penis.

In one embodiment cilostazol is administered. It is contemplated that cilostazol be administered cutaneously, transurethrally, by standard injection, intracavernosally, intranasally or through respiratory inhalation, although it is not intended that the methods of the present invention be limited to the mode of administration of cilostazol. In one embodiment, cilostazol is administered as a tablet. In another embodiment, cilostazol is administered as a pharmaceutical composition.

While the present invention is not limited to the treatment of a particular patient group, it is contemplated that the methods of the present invention comprise the utilization of pharmaceutical compounds and compositions to patients who are free of symptoms of cardiac disease and who have not been treated with drugs which cause hypotensive effects, such as nitrites and nitrates. In some embodiments, cilostazol may potentiate the hypotensive effects of nitrates, and its administration to patients who are concurrently using organic nitrates in any form may be contraindicated.

DIAGNOSIS OF MALE ERECTILE DYSFUNCTION

Determination whether a human male is suffering from impotence that is substantially only neurogenic or psychogenic is readily made by a person skilled in the art using a number of readily available diagnostic procedures. Thus, a male suffering from impotence can first be given a physical examination with particular attention to possible penile and scrotal pathology, whereby any anatomical deficiency precluding an erection sufficient for vaginal penetration can be detected. In the absence of such an anatomical deficiency, the male can be subjected to tests, whereby penile venous leakage or severe or untreatable atherosclerosis can be detected.

Such tests include determination of the penobrachial blood pressure index (PBPI), doppler investigation of the penile arteries, and a papaverine test. The PBPI is the penile systolic blood pressure divided by the systolic blood pressure determined at one of the arms. These blood pressures can be determined by any number of standard techniques. Thus, the penile systolic blood pressure can be determined by i) placing an inflatable cuff around the base of the free part of the penis in the flaccid state which is capable of being used to apply variable pressure, readable from a gauge, to an object around which the cuff is placed, ii) localizing the penile arteries with a Doppler ultrasound probe (e.g., 8 MHz probe, such as the Mini Doplex D500 available from Huntleigh Technology, Luton, United Kingdom), and then iii) inflating and deflating the cuff and ascertaining the pressure at which the Doppler sound reappears.

The pressure at which the Doppler sound reappears is the penile systolic blood pressure. A male's penile blood pressure is regarded as normal if his PBPI is >0.80. With regard to Doppler investigation, each of the two penile cavernous arteries is investigated distal to the aforementioned cuff using the Doppler ultrasound problem. The function of each of the two arteries is assessed by Doppler ultrasound using an arbitrary scale of 0, 1, 2 or 3, where 0 means that the function is so deficient that the artery cannot be located and 3 means that the artery is well enough that maximal Doppler sound is observed.

In the papaverine test, a tourniquet is placed at the base of the free part of the penis and tightened and then, with the patient seated, 30 mg of papaverine in 1 ml of a physiologically acceptable fluid (e.g., physiological saline or phosphate-buffered saline) is injected into the penile cavernous body. In persons suspected of having impotence due to a suprasacral nerve lesion or a psychogenic dysfunction, only 15 mg of papaverine is administered, because of the high incidence of papaverine-induced priapism in such cases.

Five minutes after the injection, the tourniquet is removed and an ultrasound Doppler investigation of the penile cavernous arteries is carried out as described above. The function of the arteries is regarded as normal if both of them score a 3 on the arbitrary scale. After the Doppler investigation, penile vibration, at about a 4 Hz with an amplitude of about 1.2 mm (carried out with, e.g., a Vibrector, from Multicept, Gentofte, Denmark) is carried out for five to ten minutes and then erectile response is evaluated.

Erectile response is classified as full rigidity, if the angle between the penis and the legs in the standing position is >90°, and tumescence or no response if the angle is less than or equal to 45°. An impotent male, who does not have an anatomical deficiency that would preclude having an erection sufficient for vaginal penetration, who has a PBPI >0.80, who has scores of 2 or 3 in Doppler ultrasound investigations of both of the cavernous arteries of the penis, after papaverine injection as described above, and who has a fully rigid erection after papaverine injection and vibration as described above, is suffering from impotence that is "substantially only neurogenic or psychogenic" in origin.

It is possible that atherosclerosis or venous leakage contributes to such impotence, and atherosclerosis likely does contribute if the score is less than 3 in the Doppler investigation of one or both of the cavernous arteries after papaverine injection; but any venous leakage or atherosclerosis in such impotence is not untreatable and, consequently, is not a substantial factor in the impotence and such atherosclerosis, if any, is less than severe.

Impotence, which is a side-effect of drugs such as beta-blockers, is deemed to be neurogenic impotence in the present specification. Similarly, impotence which is a result of alcoholism or excessive consumption of alcohol, is deemed to be neurogenic or psychogenic impotence, for purposes of the present specification. Thus, a male who is diagnosed in accordance with the present specification as suffering from impotence that is "substantially only neurogenic or psychogenic" in origin is suffering from impotence that is substantially only neurogenic, psychogenic or neurogenic and psychogenic in origin, even though an underlying cause of the impotence has been identified as a side-effect of a drug, alcoholism or excessive consumption of alcohol.

Generally, a male with a PBPI less than about 0.60, with scores of 0 in Doppler investigations of both penile cavernous arteries (after papaverine injection as described above), and with a less than fully rigid erection after papaverine injection and vibration will have impotence caused by "untreatable" atherosclerosis. Methods are available to ascertain whether impotence is untreatable because of venous leakage.

One method of ascertaining whether untreatable venous leakage is a cause of impotence is by cavemosometry, optionally supplemented with cavernosography. [See, e.g., Delcour et al., Radiology 161:799 (1986); Porst et al., J Urol. 137:1163 (1987); Lue et al., J. Urol. 37:829 (1987)]. Cavernosometry can be done using, both before and after intracavernosal injection of 60 mg of papaverine (in 1 ml of physiological saline), infusion of physiological saline through a 19-gauge needle into one corpus cavernosum with a 21-gauge needle inserted into the other corpus cavernosum for measurement of intracorporal pressure (which is recorded on a plotter).

The infusion rates needed to induce and maintain an erection are measured. If the infusion rate needed to maintain an erection is greater than 50 ml/min before administration of the papaverine and greater than 15 ml/min after administration of the papaverine, untreatable venous leakage is present. As long as an erection can be achieved at some flow rate less than about 100 ml/min before injection of the papaverine and less than about 50 ml/min after the injection of papaverine, it might be possible, using cavernosography, to locate the venous lesion associated with the leakage, and thereby confirm the diagnosis based on cavernosometry and provide information for possible surgical correction for the leakage. In the cavernosography, the penis is X-rayed, both before and after intracavernosal injection of 60 mg papaverine (in 1 ml of physiological saline), while infusing contrast medium into the corpus cavernosum (e.g., through a 19-gauge needle) at a flow rate that maintains an erection during the X-ray. Numerous contrast media suitable for the procedure are available in the art; these are typically aqueous solutions of iodinated compounds that provide between about 180 mg/ml and about 360 mg/ml of iodine. Examples are a solution of iohexol providing 240 mg/ml of iodine sold by Winthrop Pharmaceuticals, New York, N.Y., USA, and a solution of iopamidol providing 300 mg/ml iodine sold by Astra Meditec, Goteborg, Sweden. Typically 50–100 ml of the contrast medium will be employed for each x-ray (i.e., before and then after the injection of papaverine). In the cavernosometry and cavernosography, 30 mg papaverine (in 1 ml physiological saline) coupled with stimulation by vibration can be employed in place of 60 mg papaverine (in 1 ml physiological saline).

TREATMENT OF MALE ERECTILE DYSFUNCTION

It is not intended that the present invention be limited by the particular nature of the therapeutic preparation. For example, cilostazol can be provided together with physiologically tolerable liquid, gel or solid carriers, diluents, adjuvants and excipients. In addition, cilostazol formulations may also contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like.

The present invention is not limited by the method of introduction of the therapeutic compound to the body. Among other methods, the present invention contemplates administering cutaneously, orally, intracavemosally, transurethrally, by standard injection, intranasally or through respiratory inhalation.

While the present invention is not limited to a specific dosage level, a single dosage per day of 100 milligrams for adult humans is contemplated. Multiple dosage is also contemplated. In another embodiment, a dosage of less than 100 milligrams per day is contemplated (i.e., 50 to 75 milligrams).

Peak plasma concentrations of cilostazol are observed 2–4 hours following oral administration (See e.g., Suri et al., J. Clin. Pharmacol. 38: 144–150 [1998]; Niki and Mori, Arzneimittelforschung 35: 1173–1185 [1985]).

While the present invention is not limited by the form of oral administration, aqueous and organic solutions of cilostazol for oral administration are contemplated. Likewise, cilostazol can be associated with a solid pharmaceutical carrier for solid oral administration. The compositions may be formulated in a manner known to one skilled in the art, using pharmaceutically acceptable carriers suitable for use in such compositions that are also well known in the art. It is contemplated that the compositions of the present invention comprise 0.1–90% by weight of cilostazol. In one embodiment, cilostazol can be prepared in tablet form by mixing cilostazol with an inert diluent such as lactose (See e.g., U.S. Pat. No. 5,627,191 to Birch et al., hereby incorporated by reference). In one preferred embodiment, cilostazol is administered as a tablet.

Cilostazol may also be administered cutaneously in a carrier adapted for topical administration. Such carriers include creams, ointments, lotions, pastes, jellies, sprays, aerosols, bath oils, or other pharmaceutical carriers which accomplish direct contact between cilostazol and the pore of the skin. In some cases it may be necessary to dissolve cilostazol in an appropriate organic solvent to facilitate incorporation into a pharmaceutical preparation. One skilled in the art is able to readily prepare such pharmaceutical formulations (See e.g., U.S. Pat. No. 5,719,197 to Kanios et al., hereby incorporated by reference).

Likewise, the present invention can be incorporated in other products associated with sexual activity. For example, a coated, erection inducing condom as disclosed in U.S. Pat. No. 4,829,991, hereby incorporated by reference, can be utilized with cilostazol.

While the present invention is not limited by a specific method of introducing cilostazol intracavemosally, injection of cilostazol can be carried out by any conventional injection means (e.g., employing an hypodermic syringe and needle or a similar device such as the NovolinPen. sold by Squibb-Novo, Inc., Princeton, N.J., USA). This injection may be by subject injecting himself or by another person (such as a partner during sexual relations or a physician prior to sexual relations) injecting the male whose erection is to be induced. Methods for intracavemosal injection are described in U.S. Pat. No. 5,447,912 to Gerstenberg et al., hereby incorporated by reference.

Cilostazol can be introduced intracavemosally in a physiologically acceptable composition. Such compositions are aqueous solutions that are physiologically acceptable for administration by intracavemosal injection into the penis. The physiologically acceptable carrier is selected such that it is not painful or irritating upon intracavernosal injection. The physiologically acceptable compositions will preferably be sterile at the time of administration by intracavernosal injection.

Among the physiologically acceptable compositions for use in the methods is physiological saline or phosphate buffered saline, in which cilostazol is dissolved or suspended, such that the resulting composition is suitable for intracavernosal injection.

In carrying out the methods, it is preferred that, for a period of time between about 1 minute and about 15 minutes (preferably about 5 minutes-10 minutes), the penis is constricted near the base thereof and between the base and the point at which the injection into a corpus cavernosum occurs, in order to limit loss of injected fluid from the corpus cavernosum before the ingredients in the fluid, that are active in inducing erection, have been able to have erection-inducing effects. The constriction can be effected by any means known in the art, such as with a tourniquet, cuff, rubber band or the like, or even manually, in order to slow the release of the injected fluid and the pharmacologically active substance(s) therein into the general circulation.

Likewise, the present invention is not limited by a particular method for introducing cilostazol transurethrally. In one embodiment, cilostazol is introduced to the urethra in a carrier as described for cutaneous administration. Devices and methods for transurethral introduction of pharmaceutical compositions is described in U.S. Pat. No. 5,474,535 to Place et al.; Voss, U.S. Pat. No. 4,801,587 and Kock, EPA 0357581, all hereby incorporated by reference.

Additional methods of introducing cilostazol transurethrally include the use of medicated catheters, such as those used to prevent or treat localized infections and irritation of the urethra and bladder (See U.S. Pat. No. 4,640,912, hereby incorporated by reference). Alternatively, transurethral administration of pharmaceutical compositions is presented in U.S. Pat. Nos. 4,478,822, 4,610,868, 4,640,912 and 4,746,508, all hereby incorporated by reference, and medicated urethral suppositories, inserts or plugs, typically containing anti-infective agents or spermicide are disclosed in U.S. Pat. Nos. 1,897,423, 2,584,166, 2,696,209 and 3,373,746, all incorporated by reference.

While the present invention is not limited to the method of injecting cilostazol in the preferred embodiment, cilostazol is injected with a standard syringe. One skilled in the art would be capable of injecting cilostazol with a carrier as described for intracavernosal injection.

Cilostazol may also be administered intranasally. Formulations suitable for intranasal administration include ointments, creams, lotions, pastes, gels, sprays, aerosols, oils and other pharmaceutical carriers which accomplish direct contact between cilostazol and the nasal cavity. Examples of pharmaceutical compositions administered intranasally are described in U.S. Pat. Nos. 5,393,773 and 5,554,639 to Craig et al.; 5,603,943 to Yanagawa; and 5,801,161 to Merkus, all hereby incorporated by reference.

Cilostazol may also be administered through respiratory inhalation. Formulations suitable for respiratory inhalation include ointments, creams, lotions, pastes, gels, sprays, aerosols, oils and other pharmaceutical carriers which accomplish direct contact between cilostazol and the respiratory tract. Examples of pharmaceutical compositions administered through respiratory inhalation are described in U.S. Pat. Nos. 4,552,891 to Hu et al.; 5,869,479 to Kreutner et al., and 5,864,037 to Chasis et al.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to patients can be accomplished via aerosolization. Alternatively, the agent may be administered to the lung through a bronchoscope. Of course, the therapeutic agents may be investigated for their efficacy via other routes of administration, including parenteral administration.

In one embodiment, the administration of the compositions of the present invention is accompanied by sexual stimulation to induce an erection. The sexual stimulation can begin before or after the introduction of cilostazol. If the stimulation begins after the injection, it is preferably begun within 5 to 10 minutes to insure that there is significant overlap of the pharmacological effects of the pharmaceutical composition administered and the stimulative effects of the sexual stimulation. Whether the stimulation begins before or after the injection, it will continue preferably at least until an erection sufficient for vaginal penetration is achieved.

Sexual stimulation as prescribed by these methods, includes any form of sexual stimulation that would induce an erection in a normal male who is not suffering from erectile insufficiency. The sexual stimulation can be that which occurs in the course of sexual relations between the subject and another person or can be outside sexual relations with another person. Examples of methods of sexual stimulation include, alone or in combination, touching or erotically manipulating erogenous areas of the genital organs or other erogenous parts of the body; providing visual stimulation, as with a sexually explicit media (e.g., pornographic film) or other form of sexually stimulative show or display. Additionally, providing vibratory stimulation to the penis, at between about 30 Hz and about 100 Hz with an amplitude of about 1 mm to about 5 ram, as can be provided, for example, by resting the penis on the table of a vibrating apparatus such as that of a Vibrector system (Multicept, Genofte, Denmark).

In inducing an erection in an impotent male outside of sexual relations, as, for example, when a physician induces an erection in a patient suffering from psychogenic impotence, a preferred method of sexual stimulation includes providing visual stimulation, as with a pornographic film, simultaneously with vibratory stimulation of the penis, as with a Vibrector system set to between about 30 Hz and about 60 Hz (usually about 50 Hz)in frequency and between about 1 mm and about 2.5 mm (usually about 2.2 mm) in amplitude.

From the above, it should be clear that the present invention provides methods of treatment of male erectile dysfunction with pharmaceutical agents. In particular, cilostazol is administered therapeutically to patients having such dysfunction.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

I claim:

1. A method, comprising:
    a) providing:
        i) a patient suffering from symptoms of sexual dysfunction, and
        ii) cilostazol; and
    b) administering said cilostazol to said patient such that such symptoms are reduced.

2. The method of claim 1, wherein said administering step is orally.

3. The method of claim 1, wherein said administering step is cutaneously.

4. The method of claim 1, wherein said administering step is intranasally.

5. The method of claim 1, wherein said administering step is through respiratory inhalation.

6. The method of claim 1, wherein said administering step is by injection.

7. The method of claim 1, wherein said cilostazol is administered as a pharmaceutical composition.

8. The method of claim 1, wherein said cilostazol is administered as a single dosage of 100 milligrams per day.

9. The method of claim 1, wherein said cilostazol is administered as a tablet.

10. The method of claim 1, wherein said patient is male.

11. The method of claim 1, wherein said patient is female.

12. The method of claim 1, wherein said patient is free of cardiac disease.

13. The method of claim 1, wherein said patient is not being treated with a drug that causes hypotensive effects.

14. The method of claim 1, wherein said patient is not being treated with nitrates or nitrites.

15. A method, comprising:
    a) providing:
        i) a patient suffering from symptoms of sexual dysfunction, wherein said patient is not being treated with nitrates and
        ii) cilostazol; and
    b) administering said cilostazol to said patient such that said symptoms are reduced.

16. The method of claim 15, wherein said administering step is by injection.

17. The method of claim 15, wherein said administering step is by oral administration.

* * * * *